United States Patent [19]
Gluchowski

[11] Patent Number: 5,252,595
[45] Date of Patent: Oct. 12, 1993

[54] METHOD FOR REDUCING OR MAINTAINING INTRAOCULAR PRESSURE IN THE MAMMALIAN EYE BY ADMINISTERING PHARMACEUTICAL COMPOSITIONS CONTAINING 2-(2-ALKYLPHENYLAMINO)-OXAZOLINES, 2-(2-ALKYLPHENYL-AMINO)-THIAZOLINES AND 2-(2-ALKYLPHENYLAMINO)-IMIDAZOLINES

[75] Inventor: Charles Gluchowski, Mission Viejo, Calif.

[73] Assignee: Allergan, Inc., Irvine, Calif.

[21] Appl. No.: 926,252

[22] Filed: Aug. 5, 1992

Related U.S. Application Data

[62] Division of Ser. No. 486,381, Feb. 28, 1990, Pat. No. 5,151,440.

[51] Int. Cl.$^5$ .................. A61K 31/415; A61K 31/425
[52] U.S. Cl. .................................. 514/392; 514/370; 514/913
[58] Field of Search ................ 514/401, 392, 370, 913

[56] References Cited

U.S. PATENT DOCUMENTS

| 2,027,030 | 1/1936 | Englemann et al. | 260/44 |
| 2,876,232 | 3/1959 | Bloom | 260/307 |

(List continued on next page.)

FOREIGN PATENT DOCUMENTS

| 0451453 | 1/1988 | European Pat. Off. |
| 1191381 | 6/1963 | Fed. Rep. of Germany |
| 1195323 | 6/1963 | Fed. Rep. of Germany |
| 2127267 | 6/1971 | Fed. Rep. of Germany |
| 58-46092 | of 1983 | Japan |

OTHER PUBLICATIONS

Wollweber et al. Chem. Abstr., vol. 70, entry 47428f (1969) abstracting GB 1 132 409.

(List continued on next page.)

Primary Examiner—Zohreh A. Fay
Attorney, Agent, or Firm—Gabor L. Szekeres; Martin A. Voet; Robert J. Baran

[57] ABSTRACT

A pharmaceutical composition, preferably ophthalmic solution or ophthalmic suspension, useful for treating animals of the mammalian species, including humans, to reduce or maintain intraocular pressure in the eye contains as its pharmacologically active ingredient one or more compounds of the formula

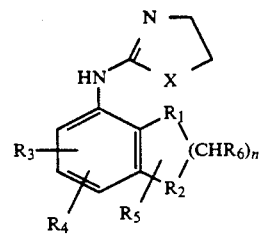

where X is O, S or NH; n is an integer with the values of 0, 1 or 2; when n is 0 then $R_1$ is lower alkyl having 1 to 6 carbon atoms and $R_2$ is H or lower alkyl having 1 to 6 carbon atoms; when n is 1 or 2, then $R_1$ and $R_2$ are methylene ($CH_2$), or methylene substituted with an $R_5$ group where $R_5$ is lower alkyl of 1 to 6 carbons; $R_3$ and $R_4$ independently are H or lower alkyl having 1 to 6 carbons; $R_6$ is H or lower alkyl of 1 to 6 carbons.

15 Claims, No Drawings

U.S. PATENT DOCUMENTS

| | | | |
|---|---|---|---|
| 3,432,600 | 3/1969 | Harvey, Jr. et al. | 424/273 |
| 3,453,284 | 7/1969 | Harvey, Jr. et al. | 260/307 |
| 3,598,833 | 8/1971 | Hiltmann et al. | 260/307 |
| 3,624,092 | 11/1971 | Levitt et al. | 260/288 |
| 3,636,219 | 1/1972 | Culik et al. | 514/291 |
| 3,679,798 | 7/1972 | Culik et al. | 424/265 |
| 3,890,319 | 6/1975 | Danielewicz et al. | 260/250 |
| 3,907,996 | 9/1975 | Griss et al. | 424/270 |
| 3,993,766 | 11/1976 | Behner et al. | 424/270 |
| 4,256,755 | 3/1981 | Smith, Jr. | 424/272 |
| 4,515,800 | 5/1985 | Cavero et al. | 514/392 |
| 4,587,257 | 5/1986 | DeSantis et al. | 514/392 |
| 4,683,229 | 7/1987 | Demarinis et al. | 514/213 |
| 5,066,664 | 11/1991 | Gluchowski | 514/377 |
| 5,091,528 | 2/1992 | Gluchowski | 544/105 |
| 5,151,440 | 9/1992 | Gluchowski | 514/377 |

OTHER PUBLICATIONS

"Heteroaromatic Analogues of the alpha$_2$-Adrenoreceptor Partial Agonist Clonidine" *J. Med. Chem.*, 1989, 32, 1627-1630, Chapleo et al.

"Possible Subdivision of Postsynaptic x-Adrenoceptors Mediating Pressor Responses in the Pithed Rat", *Nauyn-Schmiedeberg's Archives of Pharmacology*, 310, 189-193, (1979) Timmermans, et al.

"Pharmacologic Differentiation Between Pre- and Postjunctional x$_2$-adrenoceptors by SK & F 104078", *Nauyn-Schmiedeberg's Archives of Pharmacology*, 336, 415-418, (1987) Ruffolo, R., et al.

"Distribution and Function of Pheripheral-Adrenoceptors in the Cardiovascular System", Pharmacology Biochemistry & Behavior, 22, 827-833, (1985) Ruffolo, R.

"Clonidine and Related Analogues. Quantitative Correlations", *Journal of Medicinal Chemistry*, vol. 19, No. 8, pp. 1049-1053, (1976) B. Rouot, et al.

METHOD FOR REDUCING OR MAINTAINING INTRAOCULAR PRESSURE IN THE MAMMALIAN EYE BY ADMINISTERING PHARMACEUTICAL COMPOSITIONS CONTAINING 2-(2-ALKYLPHENYLAMINO)-OXAZOLINES, 2-(2-ALKYLPHENYL-AMINO)-THIAZOLINES AND 2-(2-ALKYLPHENYLAMINO)-IMIDAZOLINES

CROSS-REFERENCE TO RELATED APPLICATION

The present application is a divisional of application Ser. No. 07/486,381, filed Feb. 28, 1990, which has issued as U.S. Pat. No. 5,151,440.

BACKGROUND OF THE INVENTION

1. Field of the Invention

The present invention is directed to pharmaceutical compositions, primarily ophthalmic solutions or ophthalmic suspensions, comprising as active ingredients one or more 2-(2-alkylphenylamino)-oxazoline, 2-(2-alkylphenylamino)-thiazoline or 2-(2-alkylphenylamino)-imidazoline compounds. The pharmaceutical compositions are useful for reducing or maintaining intraocular pressure in animals of the mammalian species. In another aspect, the present invention is directed to administering such formulations and compositions to animals of the mammalian species (including humans) for reducing or maintaining intraocular pressure in the eye.

2. Brief Description of the Prior Art

Compounds useful for reducing or maintaining intraocular pressure are known in the art. Such compounds are used for treating eye diseases which manifest themselves in excessive intraocular pressure. In other words, such compounds are useful for treating glaucoma and related syndromes. That glaucoma is a serious health problem, afflicting approximately 2 percent of the population over the age of fourty years, is well known in medical science.

U.S. Pat. No. 4,515,800, for example, describes the use of 2-(trisubstituted phenylimino)imidazoline compounds [also known as 2-(trisubstituted-anilino)-1,3-diazacyclopentene-(2) compounds] in pharmaceutical compositions, preferably in eye drops, for the treatment of glaucoma.

Another aspect to the background of the present invention is in the field of heterocyclic chemistry, primarily as such chemistry is practiced for the purposes of developing biologically active compounds. In this regard, the following United States and foreign patents, which describe substituted oxazoline, thiazoline and imidazoline compounds, comprise further background to the present invention:

U.S. Pat. No. 3,598,833 [2-cycloalkylamino oxazolines having local anesthetic, sedative, vasoconstrictory, mucous membrane de-swelling, blood pressure depressant and gastric fluid secretion inhibitory effects];

U.S. Pat. No. 4,587,257 [2-(trisubstituted phenylimino)imidazoline compounds capable of controlling ocular bleeding];

U.S. Pat. No. 3,636,219 [2-(substituted-phenylamino)-thiazolines and imidazolines having anticholinergic activity];

U.S. Pat. No. 3,453,284 [2-(substituted-anilino)-2-oxazolines;

U.S. Pat. No. 3,432,600 [partially reduced 2-(naphthylamino) oxazolines and indanylamino oxazolines;

U.S. Pat. No. 3,679,798 [compositions comprising arylaminooxazolines and an antocholigeneric agent];

U.S. Pat. No. 3,624,092 [amino-oxazolines useful as central nervous system depressants];

U.S. Pat. No. 2,876,232 [2-(9-fluorenylamino)oxazolines,) and German Patent Nos. 1,191,381 and 1,195,323, and European Patent Application No. 87304019.0.

As it will become apparent from the ensuing description, some of the "composition of matter" used in the novel pharmaceutical compositions and methods of administration of the present invention are described or mentioned in one or more of the above-listed references, but the activity of these compounds as agents for reducing or maintaining intraocular pressure in animals of the mammalian species is believed to be novel to the present invention.

SUMMARY OF THE INVENTION

The present invention covers pharmaceutical compositions, primarily ophthalmic solutions and ophthalmic suspensions, which comprise as active agents for maintaining or reducing intraocular pressure (anti-glaucoma agents) one or more compounds having the formula

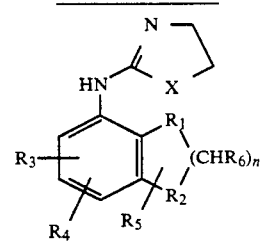

FORMULA 1 where X is O, S or NH; n is an integer with the values of 0, 1 or 2; when n is 0 then $R_1$ is lower alkyl having 1 to 6 carbon atoms and $R_2$ is H or lower alkyl having 1 to 6 carbon atoms; when n is 1 or 2, then $R_1$ and $R_2$ are methylene ($CH_2$), or methylene substituted with an $R_5$ group where $R_5$ is lower alkyl of 1 to 6 carbons; $R_3$ and $R_4$ independently are H or lower alkyl having 1 to 6 carbons; $R_6$ is H or lower alkyl of 1 to 6 carbons. The pharmaceutical compositions, preferably ophthalmic solutions or ophthalmic suspensions containing one or more of the above-defined compounds as active ingredients, are administered to animals of the mammalian species for the purpose of reducing or maintaining intraocular pressure in the eye.

GENERAL EMBODIMENTS

Definitions

The term "alkyl" as used here refers to and includes normal and branch chained alkyl groups as well as cycloalkyl groups. The term "lower alkyl", unless specifically stated otherwise, includes normal alkyl, branch chained alkyl as well as cycloalkyl groups having 1 to 6 carbon atoms.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

With reference to Formula 1, in the compounds which are preferably incorporated into the pharmaceutical compositions or formulations of the present invention, and which are used in the method of administering such formulations to animals and humans for the purpose of maintaining or reducing intraocular pressure in the eye, preferably the $R_3$, $R_4$ and $R_6$ groups are H. Preferably n is zero, and in that case the $R_1$ and $R_2$ groups preferably are, independently from one another, lower alkyl having 1 to 3 carbons. Active agents in the novel pharmaceutical compositions and in the novel method of administration of the present invention are also preferred where, in accordance with Formula 1, n is 2 and the $R_1$ and $R_2$ groups both are $CH_2$, there is no $R_5$ substituent and $R_6$ is H. Preferably, the active compounds in the composition and method of administration of the present invention are oxazoline and imidazoline derivatives: i.e. preferably in Formula 1 X is O or NH.

Most preferred as active agents in the novel compositions and methods of administration of the present invention are oxazoline or imidazoline compounds where: $R_3$ and $R_4$ are both H, and (1) n is 0 and $R_1$ and $R_2$ both are $CH_3$, or (2) n is 2 and $R_1$ and $R_2$ both are $CH_2$, there is no $R_5$ substituent and $R_6$ is H. The compounds which are most preferred as active ingredients in the composition and method of administration of the present invention, in accordance with the foregoing, are illustrated in Formula 2:

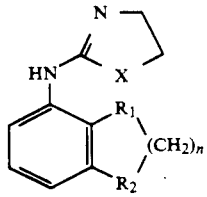

Formula 2

Compound 1 X=O n=0, $R_1$=$R_2$=$CH_3$,
Compound 2 X=O n=2, $R_1$=$R_2$=$CH_2$,
Compound 3 X=NH n=0, $R_1$=$R_2$=$CH_3$, and
Compound 4 X=NH n=2, $R_1$=$R_2$=$CH_2$.

For maintaining intraocular pressure in a mammalian eye, and particularly for reducing such pressure (as for treatment of glaucoma in humans suffering from that condition) the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water) saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 1% (weight per volume) and more preferably approximately 0.05% to approximately 0.5% (weight per volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topicallly to the eye.

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Active Compound in accordance with the invention, | about 0.0001 to about 1.0 |
| Preservative | 0–0.10 |
| Vehicle | 0–40 |
| Tonicity Adjuster | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

The anti-glaucoma activity (ability to maintain or reduce intraocular pressure) of the active compounds in accordance with the present invention, was confirmed by the following assay procedure. This assay procedure is generally recognized in the art to provide pertinent information with respect to the anti-glaucoma activity of the formulations assayed. Thus, each of the compounds to be tested was dissolved in distilled water at a concentration of 0.1% (W/V). Each of these solutions was administered topically and unilaterally to one eye of a drug-naive, unanesthetized New Zealand white rabbit in a single 50 micro liter drop. The contralateral eye received an equal volume of saline prior to determining the intraocular pressure after the mixture was administered Also, approximately 10 micro liters of 0.5% (W/V) proparacaine (topical anesthetic) was applied to the corneas of each of the rabbits before determining intraocular pressure. As a control test, six (6) other drug-naive, unanesthetized New Zealand white rabbits were treated and tested as described above except that no compound to be tested was included in the solutions administered to the eyes.

The intraocular pressure was determined in both eyes of each rabbit both before and after the solutions were administered. Such intraocular pressure determinations were made in the conventional manner using conventional equipment.

Results of these IOP determinations were as follows:

| | Maximum Difference in Intraocular Pressure After Solution Administration mm Hg | |
|---|---|---|
| Example | Ipsilateral (Treated Eye) | Contralateral (Untreated) Eye |
| Control | N.S. | N.S. |
| Compound 1 | −3.6 ± 0.08 | −6.4 ± 1.2 |
| Compound 2 | −3.8 ± 1.1 | −6.4 ± 1.0 |
| Compound 3 | −2.4 ± 0.9 | −4.6 ± 1.1 |
| Compound 4 | −2.6 ± 0.9 | −4.6 ± 0.6 |

N.S. refers to no significant change in the intraocular pressure.

These results demonstrate the effectiveness in reducing intraocular pressure achieved by directly administering the compounds, discovered in accordance with the present invention to be active, to mammalian eyes. In addition, at least with regard to certain mammalian eyes, e.g., New Zealand white rabbit eyes, the intraocular pressure in the contralateral eye is also reduced, and with respect to certain examplary compounds in accordance with the invention, the reduction in the contralateral eye is greater than in the ipsilateral eye.

SPECIFIC EMBODIMENTS

The compounds which were found in accordance with the present invention to be active for maintaining or reducing intraocular pressure, can be made by a number of different synthetic chemical pathways. To illustrate the invention, there is here outlined a series of steps which have been proven to provide the active compounds of Formula 1, when such synthesis is followed in fact and in spirit. The synthetic chemist will readily appreciate that the specific conditions set out here can be generalized to any and all of the compounds represented by Formula 1. Furthermore, the synthetic chemist will readily appreciate that the herein described synthetic steps may be varied and or adjusted by those skilled in the art, to obtain the active compounds used in the novel pharmaceutical composition and method of administration of the present invention.

Active oxazoline compounds (in Formula 1 X=0) used in the pharmaceutical compositions and methods of administration of the present invention, where n=0 and where $R_1$ is lower alkyl of 1 to 6 carbons, $R_2$ is H or lower alkyl of 1 to 6 carbons, and where $R_3$ and $R_4$ are defined as above in connection with Formula 1, can be synthesized in accordance with the generalized procedure shown in Reaction Scheme 1.

As a first step of this reaction sequence, an aniline derivative corresponding to Formula 3 (where $R_1$ is lower alkyl of 1 to 6 carbons, $R_2$ is H or lower alkyl of 1 to 6 carbons, and where $R_3$ and $R_4$ are defined as in connection with Formula 1) is reacted with chloroethylisocyanate (Compound 5, a commercially readily available reagent). The reaction between compounds of Formula 3 and chloroethylisocyanate (Compound 5) is typically conducted in a neutral solvent, such as tetrahydrofuran (THF) and may be conducted at room temperature or at elevated temperature. In the event the aniline derivative (compound of Formula 3) is added to the reaction as a hydrochloride (or like) salt, an acid acceptor (such as triethylamine) may also be added to the reaction mixture.

REACTION SCHEME 1

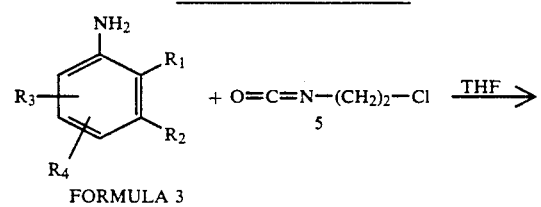

FORMULA 3

-continued
REACTION SCHEME 1

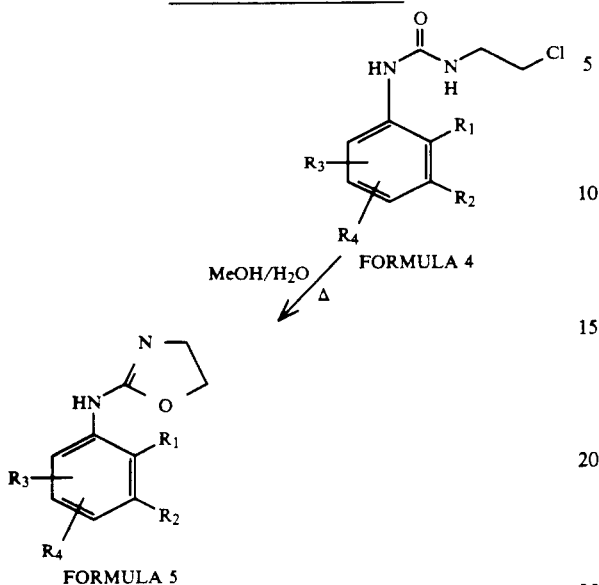

FORMULA 4

FORMULA 5

-continued
SCHEME 2

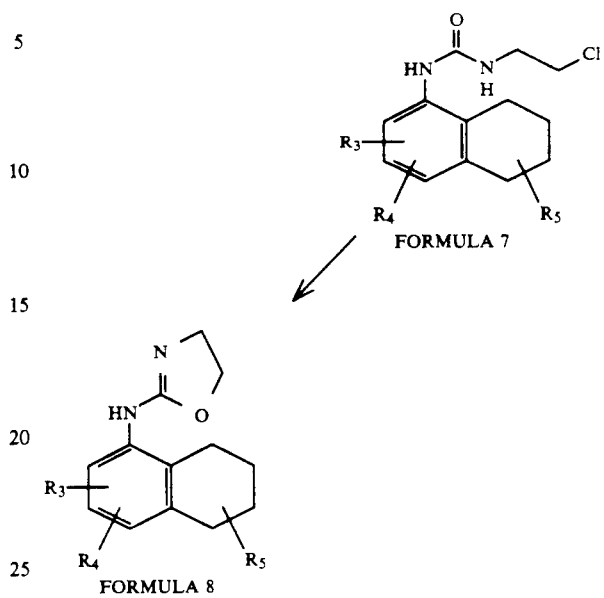

FORMULA 7

FORMULA 8

The reaction between chloroethylisocyanate (Compound 5) and the aniline derivative of Formula 3 provides the intermediate chloroethylurea derivative, compound of Formula 4 ($R_1$ is lower alkyl of 1 to 6 carbons, $R_2$ is H or lower alkyl of 1 to 6 carbons, and where $R_3$ and $R_4$ are defined as above in connection with Formula 1). The chloroethylurea derivative (Formula 4) typically precipitates out of the reaction mixture, and is isolated, for example by vacuum filtration. Generally speaking, the chloroethylurea derivative (Formula 4) can be adequately characterized and used in the next reaction without further purification.

The chloroethylurea derivative (Formula 4) is cyclized to provide the desired 2-(alkylphenylamino) oxazolines (Formula 5) by heating, preferably in an aqueous medium, such as a solvent mixture containing water and a lower alcohol, preferably methanol. Typically, the desired 2-(alkylphenylamino) oxazoline (Formula B)obtained in the cyclization reaction, is isolated from the reaction mixture by first concentrating the same to remove the solvents, and thereafter by extraction in halogenated organic solvent (such as methylene chloride) followed by evaporation of the organic solvent. The desired product may also be recrystallized to attain further purity. The desired 2-(alkylphenylamino) oxazolines (Formula 5) may also be isolated from the cyclization reaction as the corresponding hydrochloride (or other) salt. For preparation of 2-(alkylphenylamino) oxazolines in general, and of compound 1 in particular, further reference is made to U.S. Pat. No. 3,453,284, the specification of which is expressly incorporated herein by reference.

2-(5,6,7,8-Tetrahydronaphthylamino)-oxazoline derivatives (in Formula 1 X=O n=2), which in accordance with the present invention are active agents for reducing or maintaining intraocular pressure in mammals, can be made from the corresponding 5,6,7,8-tetrahydronaphthyl-1-amine, or substituted 5,6,7,8-tetrahydronaphthyl-1-amine, (compounds of Formula 6) by reaction with chloroethylisocyanate (Compound 5) as illustrated in Reaction Scheme 2. The conditions of this reaction are substantially similar to the analogous reaction described above with reference to Reaction Scheme 1. The resulting chloroethylurea intermediates (compounds of Formula 7) are cyclized into the desired 2-(5,6,7,8-tetrahydronaphthylamino)-oxazoline derivatives (Formula 8) by heating in a polar solvent, such as aqueous methanol. In Formulas 6, 7 and 8 the symbols $R_3$, $R_4$ and $R_5$ are defined as in connection with Formula 1. For preparation of 2-(5,6,7,8-tetrahydronaphthylamino)-oxazoline derivatives in general, and of Compound 2 in particular, further reference is made to U.S. Pat. No. 3,432,600, the specification of which is expressly incorporated herein by reference.

SCHEME 2

FORMULA 6

SCHEME 3

FORMULA 9

-continued
SCHEME 3

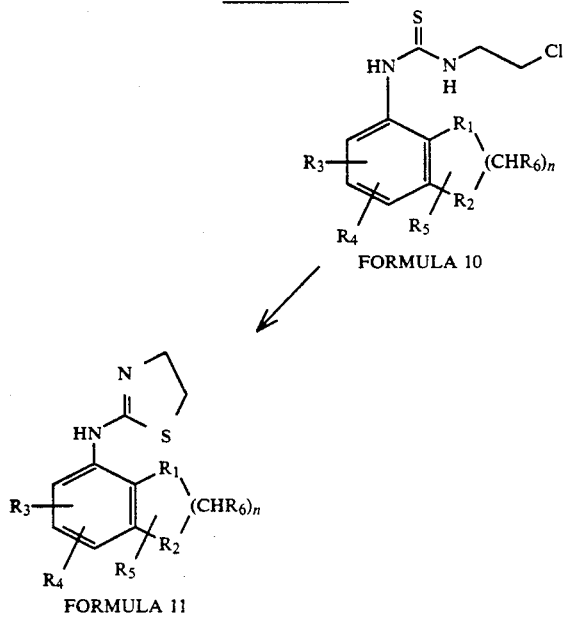

2-(2-Alkylphenylamino)-thiazolines (i.e. compounds where in Formula 1 X=S) which are active in accordance with the present invention for reducing or maintaining intraocular pressure in mammals, can be synthesized in a reaction sequence which is analogous to the reaction sequences outlined above for the corresponding oxazoline derivatives; the only significant difference being that in the first step of the sequence chloroethylisothiocyanate (compound 6) is used (instead of chloroethylisocyanate, Compound 5). Thus, referring to generalized Reaction Scheme 3, an alkyl substituted aniline corresponding to Formula 9 is reacted with chloroethylisothiocyanate (Compound 6) in a suitable solvent, (such as tetrahydrofuran) to provide the intermediate chloroethylthiourea (Formula 10). The symbols n and $R_1$ through $R_6$ in the formulas illustrated in Reaction Scheme 3 are defined as above with reference to Formula 1. In this connection it is noted that Formula 9 embraces substituted and unsubstituted 5,6,7,8-tetrahydro-1-naphthylamines, and that, in this specification with reference to the aromatic moiety of the active compounds used in the invention, the terms an "alkyl substituted phenyl" or "alkyl substituted aniline" broadly cover 5,6,7,8-tetrahydronaphthyl derivatives as well. Referring still to Reaction Scheme 3 the intermediate chloroethylthiourea (Formula 10) is cyclized, typically in an aqueous solvent mixture (e.g. $H_2O$ and $CH_3OH$) at room temperature or by gentle heating, to provide the desired 2-(2-alkylphenylamino)-thiazolines (Formula 11).

2-(2-Alkylphenylimino)-imidazolidines (i.e. compounds of Formula 1 where X=NH) which have been discovered in the present invention to be active as agents for reducing or maintaining intraocular pressure in mammals, can be synthesized, generally speaking, by the reaction of imidazoline-2-sulfonic acid (Compound 7) with an appropriately substituted aniline. Imidazoline-2-sulfonic acid (Compound 7) can be made in accordance with the procedure described in the chemical literature, (e.g. U.S. Pat. No. 4,656,291) from 2-imidazolidinethione (Compound s) The synthetic steps leading to 2-(5,6,7,8-tetrahydro-1-naphthylimino)-imidazolidines [2-(5,6,7,8-tetrahydro-1-naphthylamino)-imidazolines] and to 2-(alkylphenylimino)-imidazolidines [2-(alkylphenylamino)-imidazolines], respectively, are illustrated in generalized Reaction Schemes 4 and 5.

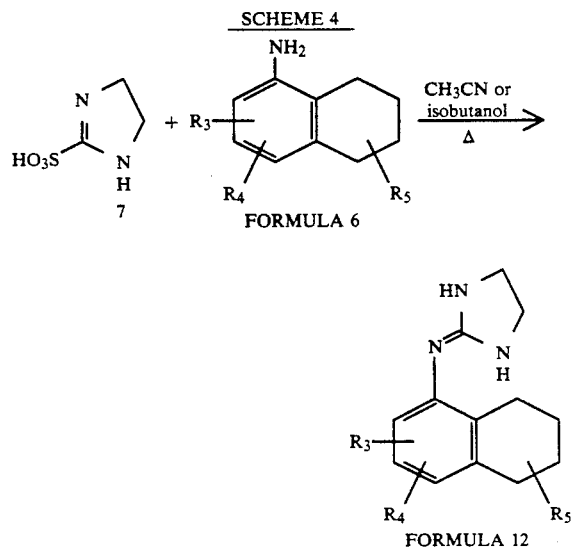

Thus, with specific reference to Reaction Scheme 4, imidazoline-2-sulfonic acid (Compound 7) is heated under pressure in a solvent (e.g. acetonitrile) with a substituted or unsubstituted 5,6,7,8-tetrahydronaphthyl-1-amine (Formula 6), to provide the 2-(5,6,7,8-tetrahydro-1-naphthylimino)-imidazolidine derivatives of Formula 12. The symbols $R_3$, $R_4$ and $R_5$ in Formula 12 are defined the same as in Formula 6.

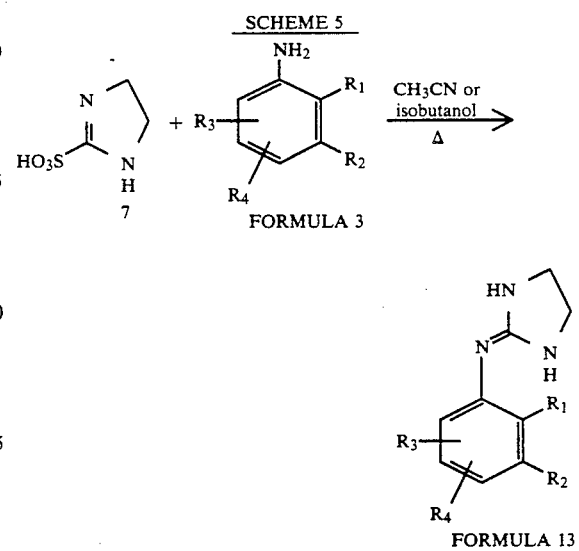

Reaction Scheme 5 illustrates the synthesis of 2-(alkylphenylimino)-imidazolidine derivatives (Formula 13) Where, with reference to Formula 1 X=NH and n=0. In this synthesis a substituted aniline of Formula 3 is heated under pressure with imidazoline-2 sulfonic acid (Compound 7). In Formula 13 the symbols $R_1$, $R_2$, $R_3$ and $R_4$ are defined as in connection with Formula 3 For further description of other syntheses of compounds of Formula 13, reference is made to U.S. Pat. No. 3,679,798, the specification of which is expressly incorporated herein.

SPECIFIC EXAMPLES 2-(2,3-Dimethylphenylamino)-oxazoline (Compound 1)

Chloroethylisocyanate (Compound 5, Aldrich, 346 mg, 3.3 mmol) was added to a stirred solution of 2,3-dimethylaniline (Aldrich, 400 mg, 3.3 mmol) in tetrahydrofuran (5 ml) at room temperature. After 30 minutes a white precipitate formed. The solid chloroethylurea was collected by vacuum filtration, yield: 477 mg (64%): mp 145°-146° C. $^1$HNMR (300 MHz, CDCl$_3$) & 7.00 (m, 3H); 6.72 (br, 1H); 5.19 (br, 1H), 3.59 (m, 2H); 3.49 (m, 2H); 2.30 (s, 3H); 2.18 (s, 3H); Mass spectrum m/e 226.0872 ($C_{11}H_{15}ClN_2O$ requires 226 0872). The chlorethylurea (199 mg, 0.88 mmol) was suspended in H$_2$O (4 ml) and CH$_3$OH (4 ml) and heated to reflux for 1 hour. The reaction mixture was cooled to room temperature and concentrated in vacuo. The residue was dissolved in CH$_2$Cl$_2$ and washed with 1N NaOH (to pH 13). The organic layer was dried over Na$_2$CO$_3$ and concentrated in vacuo to yield 140 mg (84%) of the title compound as a white crystalline solid: mp 112°-113.5° C.; $^1$H NMR (300 MHz, CDCl$_3$) & 7.19 (m, 1H); 7.09 (m, 1H), 6.91 (m, 1H); 5.00 (br s, 1H); 4.40 (t, 2H); 3.70 (t, 2H); 2.30 (s, 3H); 2.15 (s, 3H); Mass spectrum m/e 190.1104 ($C_{11}H_{14}N_2O$ requires 190.1106).

Following a substantially similar procedure and starting with the corresponding substituted aniline, the following additional samples of compounds of the invention can be synthesized, and utilized in the novel opthalmic compositions and methods of administration of the present invention:

2-(2,3-diethylphenylamino)-oxazoline;
2-(2-methyl-3-ethylphenylamino)-oxazoline;
2-(2-ethyl-3-methylphenylamino)-oxazoline;
2-(2,3,4-trimethylphenylamino)-oxazoline;
2-(2,3,5-trimethylphenylamino)-oxazoline;
2-(2,5,6-trimethylphenylamino)-oxazoline;
2-(5,6,7,8-tetrahydronaphthylamino)-oxazoline (Compound 2)

Chloroethylisocyanate (Compound 5 210 mg, 2.05 mmol) was added to a stirred solution at 5,6,7,8-tetrahydro-1-naphthylamine (302 mg, 2.05 mmol) in tetrahydrofuran (2 ml). After 30 minutes the resulting chloroethylurea was collected by vacuum filtration. Yield: 302 mg (58%) of fine white crystals: mp 101°-103°; $^1$H NMR (300 MHz, CDCl$_3$) & 6.98-7.30 (m, 3H); 6.08 (br s, 1H); 5.19 (br s, 1H); 3.68 (m, 2H); 3.55 (m, 2H); 2.79 (m, 2H); 2.61 (m, 2H); 1.80 (m, 4H); Mass spectrum m/e 252.1034 ($C_{13}H_{17}ClN_2O$ requires 252.1029). The chloroethyl urea (237 mg, 0.94 mmol) was suspended in H$_2$O (3 ml) and CH$_3$OH (3 ml) and heated to reflux for 18 hours. The reaction mixture was cooled to room temperature and worked up as above to yield after recrystallization (hexane/CHCl$_3$) 187.6 mg (87%) of the title compound: mp 160°-162° C.; $^1$H NMR (300 MHz, CDCl$_3$) & 7.23 (m, 1H); 7.08 (m, 1H; 6.75 (m, 1H); 5.55 (br, 1H); 4.35 (t, 2H); 3.70 (t, 2H); 2.70 (m, 2H); 2.58 (m, 2H); 1.80 (m, 4H); Mass spectrum m/e 216.1257 ($C_{13}H_{16}N_2O$ requires 216.1262).

Following a substantially similar procedure and start the invention can be synthesized, and utilized in the novel opthalmic compositions and methods of administration of the present invention:

2-(2-methyl-5,6,7,8-tetrahydronaphthylamino)-oxazoline;
2-(3-methyl-5,6,7,8-tetrahydronaphthylamino)-oxazoline;
2-(4-methyl-5,6,7,8-tetrahydronaphthylamino)-oxazoline;
2-(5-methyl-5,6,7,8-tetrahydronaphthylamino)-oxazoline;
2-(6-methyl-5,6,7,8-tetrahydronaphthylamino)-oxazoline;
2-(7-methyl-5,6,7,8-tetrahydronaphthylamino)-oxazoline;
2-(8-methyl-5,6,7,8-tetrahydronaphthylamino)-oxazoline;
2-(2-ethyl-5,6,7 8-tetrahydronaphthylamino)-oxazoline;
2-(3-ethyl-5,6,7 8-tetrahydronaphthylamino)-oxazoline;
2-(4-ethyl-5,6,7,8-tetrahydronaphthylamino)-oxazoline;
2-(5-ethyl-5,6,7,8-tetrahydronaphthylamino)-oxazoline;
2-(6-ethyl-5,6,7,8-tetrahydronaphthylamino)-oxazoline;
2-(7-ethyl-5,6,7,8-tetrahydronaphthylamino)-oxazoline;
2-(8-ethyl-5,6,7,8-tetrahydronaphthylamino)-oxazoline;
2-(2,3-dimethyl-5,6,7,8-tetrahydronaphthylamino)-oxazoline;
2-(2,4-dimethyl-5,6,7,8-tetrahydronaphthylamino)-oxazoline;
2-(3,4-dimethyl-5,6,7,8-tetrahydronaphthylamino)-oxazoline;
2-(2,5-dimethyl-5 6 7 8-tetrahydronaphthylamino)-oxazoline;
2-(2,6-dimethyl-5,6,7,8-tetrahydronaphthylamino)-oxazoline;
2-(2,7-dimethyl-5,6,7,8-tetrahydronaphthylamino)-oxazoline;
2-(2,8-dimethyl-5,6,7,8-tetrahydronaphthylamino)-oxazoline;
2-(3,5-dimethyl-5,6,7,8-tetrahydronaphthylamino)-oxazoline;
2-(3,6-dimethyl-5,6,7,8-tetrahydronaphthylamino)-oxazoline;
2-(3,7-dimethyl-5,6,7,8-tetrahydronaphthylamino)-oxazoline, and
2-(3,8-dimethyl-5,6,7,8-tetrahydronaphthylamino)-oxazoline.

2-(5,6,7,8-Tetrahydro-1-naphthylimino)-imidazolidine (Compound 4)

Preparation of imidazoline-2-sulfonic acid: 2-Imidazolidinethione (Compound 8, Aldrich, 66.3 g, 650 mmol), Na$_2$MoO$_4$ (5g, 227 mmol) and NaCl (15 g. 256 mmol) were added to 300 ml H$_2$O. Although some dissolution occurred, a solid residue remained in the liquid of the mixture. The mixture was cooled to −10° C. using an immersion cooler. 500 ml of a 30% (w/v) aqueous H$_2$O$_2$ solution was placed in a jacketed controlled drop rate addition funnel and cooled to 0° C. using an ice/H$_2$O bath. The aqueous H$_2$O$_2$ solution was added to the mixture at a rate of 60 drops/min. The mixture was stirred for 16 hours at −10° C. During this time, the mixture changed from a white suspension to a dark blue solution to a light blue suspension. At the end of 16 hours, a solid was filtered from the suspension and dried in vacuo. No further purification was needed. Yield: 57.8 g (a yield of 52.3%) of the title compound as a white solid mp 157°-159° C.; $^1$H NMR (300 MHz, DMSO d6) & 10.38 (br, 2H); 3.85 (s, 4H). This solid was stable when stored in the dark at 0° C. for at least 6 months.

2-(5,6,7,8-tetrahydro-1-naphthylimino)-imidazolidine (Compound 4):

5,6,7,8-Tetrahydro-1-naphthylamine (Aldrich, 159 mg, 1.06 mmol), imidazoline-2-sulfonic acid (147.0 mg, 1.0 mmol, Compound 7 obtained as described above) and $CH_3CN$ (5ml) were placed in a thick-walled cap which was sealed with a TEFLON TM screw and heated to 155° C. for 1.25 hours The reaction mixture was cooled to room temperature and concentrated in vacuo. The residue was dissolved in $CHCl_3$ and washed with aq. 1N NaOH (to pH 13). The organic layer was separated, washed with brine, dried over $Na_2CO_3$ and concentrated in vacuo to yield a brown oil The crude material was purified by flash chromatography ($SiO_2$; 80:20 $CHCl_3/CH_3OH$ saturated with $NH_3$) to yield 29.5 mg (14%) of the title compound as a white solid: mp 138°–141° C.; $^1H$ NMR (300 MHz, $CDCl_3$) & 7.05 (t, 1H) 6.82 (m, 2H); 5.41 (br, 2H); 3.50 (s, 4H); 2.79 (m, 2H); 2.62 (m, 2H); 1.80 (m, 4H); Mass spectrum m/e 214.1339 ($C_{13}H_{16}N_3$ requires 214.1344). Alternatively and preferably alcohols, most preferably isobutanol, are used instead of $CH_3CN$ in this reaction.

Following a substantially similar procedure and starting with the corresponding substituted 5,6,7,8-tetrahydronaphthyl-1-amine, the following additional examples of compounds of the invention can be synthesized, and utilized in the novel opthalmic compositions and methods of administration of the present invention:

2-(2-methyl-5,6,7,8-tetrahydronaphthylimino)-imidazolidine;
2-(3-methyl-5,6,7,8-tetrahydronaphthylimino)-imidazolidine;
2-(4-methyl-5,6,7,8-tetrahydronaphthylimino)-imidazolidine;
2-(5-methyl-5,6,7,8-tetrahydronaphthylimino)-imidazolidine;
2-(6-methyl-5,6,7,8-tetrahydronaphthylimino)-imidazolidine;
2-(7-methyl-5,6,7,8-tetrahydronaphthylimino)-imidazolidine;
2-(8-methyl-5,6,7,8-tetrahydronaphthylimino)-imidazolidine;
2-(2-ethyl-5,6,7,8-tetrahydronaphthylimino)-imidazolidine;
2-(3-ethyl-5,6,7,8-tetrahydronaphthylimino)-imidazolidine;
2-(4-ethyl-5,6,7,8-tetrahydronaphthylimino)-imidazolidine;
2-(5-ethyl-5,6,7,8-tetrahydronaphthylimino)-imidazolidine;
2-(6-ethyl-5,6,7,8-tetrahydronaphthylimino)-imidazolidine;
2-(7-ethyl-5,6,7,8-tetrahydronaphthylimino)-imidazolidine;
2-(8-ethyl-5,6,7,8-tetrahydronaphthylimino)-imidazolidine;
2-(2,3-dimethyl-5,6,7,8-tetrahydronaphthylimino)-imidazolidine;
2-(2,4-dimethyl-5,6,7,8-tetrahydronaphthylimino)-imidazolidine;
2-(3,4-dimethyl-5,6,7,8-tetrahydronaphthylimino)-imidazolidine;
2-(2,5-dimethyl-5,6,7,8-tetrahydronaphthylimino)-imidazolidine;
2-(2,6-dimethyl-5,6,7,8-tetrahydronaphthylimino)-imidazolidine;
2-(2,7-dimethyl-5,6,7,8-tetrahydronaphthylimino)-imidazolidine;
2-(2,8-dimethyl-5,6,7,8-tetrahydronaphthylimino)-imidazolidine;
2-(3,5-dimethyl-5,6,7,8-tetrahydronaphthylimino)-imidazolidine;
2-(3,6-dimethyl-5,6,7,8-tetrahydronaphthylimino)-imidazolidine;
2-(3,7-dimethyl-5,6,7,8-tetrahydronaphthylimino)-imidazolidine; and
2-(3,8-dimethyl-5,6,7,8-tetrahydronaphthylimino)-imidazolidine.

2-(2,3-Dimethylphenylimino)-imidazolidine (compound 3)

2,3 Dimethylaniline (Aldrich, 236 mg, 1.95 mmol), imidazoline-2-sulfonic acid (292 mg, 1.95 mmol, (Compound 7 obtained as described above)) and $CH_3CN$ (4ml) were placed in a thick-walled glass tube and sealed with a TEFLON TM screw-cap. The reactants were heated to 155° C. for 6 hours The reaction was worked up as described for Compound 4 and chromatographed ($SiO_2$; 70:30 $CHCl_3/CH_3OH$ saturated with $NH_3$) to yield a light yellow oil which was recrystallized (hexane/isopropanol to yield 61 mg (17%) of the title compound as an off-white crystalline solid: mp 141°–144° C.; $^1H$ NMR (300 MHz, $CDCl_3$) & 6.98 (m, 1H); 6.80 (m, 2H), 5.31 (br, 2H); 3.42 (s, 4H); 2.31 (s, 3H); 2.12 (s, 3H); Mass spectrum m/e 189.1259 ($C_{11}H_{15}N_3$ requires 189.1266). Alternatively, and preferably alcohols, most preferably isobutanol, are used instead of $CH_3CN$ in this reaction.

Following a substantially similar procedure and starting with the corresponding substituted aniline, the following additional examples of compounds of the invention can be synthesized, and utilized in the novel opthalmic compositions and methods of administration of the present invention:

2-(2,3-diethylphenylimino)-imidazolidine;
2-(2-methyl-3-ethylphenylimino)-imidazolidine;
2-(2-ethyl-3-methylphenylimino)-imidazolidine;
2-(2,3,4-trimethylphenylimino)-imidazolidine;
2-(2,3,5-trimethylphenylimino)-imidazolidine;
2-(2,5,6-trimethylphenylimino)-imidazolidine.

What is claimed is:

1. A method of treating animals of the mammalian species, including humans, for the purpose of reducing or maintaining intraocular pressure in the eye of the mammal, the method of treatment comprising the steps of administering to the mammal a pharmaceutical composition which comprises as its active ingredient one or more compounds of the formula

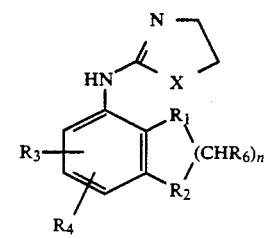

where
X is S or NH;

n is an integer with the values of 0, 1 or 2; $R_3$ and $R_4$ independently are H or lower alkyl having 1 to 6 carbons;

$R_6$ is H or lower alkyl of 1 to 6 carbons, with the proviso that when n is 0 then $R_1$ is lower alkyl having 1 to 6 carbon atoms and $R_2$ is H or lower alkyl having 1 to 6 carbon atoms, when n is 1 or 2, then $R_1$ and $R_2$ both are $CHR_5$, where $R_5$ independently is H or lower alkyl of 1 t 6 carbons, or salts of compounds of said formula, the active ingredient being present in the pharmaceutical composition in approximately 0.0001 to 1.0 percent weight by volume concentration.

2. The method of treatment of claim 1 wherein in the formula of the active ingredient n is zero.

3. The method of treatment of claim 2 wherein in the formula of the active ingredient $R_1$ and $R_2$ both are $CH_3$.

4. The method of treatment of claim 3 wherein in the formula of the active ingredient $R_3$ and $R_4$ both are H.

5. The method of treatment of claim 4 wherein in the formula of the active ingredient x is NH.

6. The method of treatment of claim 1 wherein in the formula of the active ingredient n is 2.

7. The method of treatment of claim 6 wherein in the formula of the active ingredient $R_5$ and $R_6$ both are H.

8. The method of treatment of claim 7 wherein in the formula of the active ingredient $R_3$ and $R_4$ both are H.

9. The method of treatment of claim 7 wherein in the formula of the active ingredient x is NH.

10. A method of treating animals of the mammalian species, including humans, for the purpose of reducing or maintaining intraocular pressure in the eye of the mammal, the method of treatment comprising the steps of administering directly to the eye of the mammal a pharmaceutical composition which comprises as its active ingredient one or more compounds of the formula

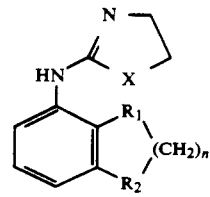

where
X is NH;
n is an integer with the values of 0, 1 or 2, with the proviso that when n is 0 then $R_1$ is lower alkyl having 1 to 6 carbon atoms and $R_2$ is H or lower alkyl having 1 to 6 carbon atoms, when n is 1 or 2, then $R_1$ and $R_2$ both are $CH_2$, or salts of compounds of said formula, the active ingredient being present in the pharmaceutical composition in approximately 0.0001 to 1.0 percent weight by volume concentration.

11. The method of treatment of claim 1 wherein in the formula of the active ingredient n is zero.

12. The method of treatment of claim 11 wherein in the formula of the active ingredient $R_1$ and $R_2$ both are $CH_3$.

13. The method of treatment of claim 12 where the composition is an ophthalmic solution or an ophthalmic suspension, adapted for administration to the eye of a mammal in the form of eye droplets.

14. The method of treatment of claim 10 wherein in the formula of the active ingredient n is 2.

15. The method of treatment of claim 14 where the composition is an ophthalmic solution or an ophthalmic suspension, adapted for administration to the eye of a mammal in the form of eye droplets.

* * * * *

UNITED STATES PATENT AND TRADEMARK OFFICE
CERTIFICATE OF CORRECTION

PATENT NO. : 5,252,595

DATED : October 12, 1993

INVENTOR(S) : Charles Gluchowski

It is certified that error appears in the above-identified patent and that said Letters Patent is hereby corrected as shown below:

Column 5, line 38, after "administered" add —.—;

Column 5, line 58, "(Treated Eye)" should be —(Treated) Eye—;

Column 9, line 67, "s)" should be —8)—;

Column 10, line 62, "Where" should be —where—;

Column 10, line 67, after "3" add —.—;

Column 11, line 17, "226 0872" should be —226.0872—;

Column 11, line 32, "samples" should be —examples—;

Column 11, line 65, "start" should be —starting with the corresponding substituted 5,6,7,8,-tetrahydronaphthyl—;

Column 12, line 66, "d6" should be —$d_6$—;

Column 13, line 9, after "hours" add —.—;

Column 13, line 14, after "oil" insert —.—;

Column 14, line 22, after "hours" add —.—;

Column 15, line 10, "t" should be —to—;

Column 15, lines 15,17,20,22,24,26,28,30, and 31, "claim" should be —Claim—

UNITED STATES PATENT AND TRADEMARK OFFICE
CERTIFICATE OF CORRECTION

PATENT NO. : 5,252,595
DATED : October 12, 1993
INVENTOR(S) : Charles Gluchowski It is certified that error appears in the above-indentified patent and that said Letters Patent is hereby corrected as shown below:

Column 16, line 24, "1" should be —10—.

Signed and Sealed this

Nineteenth Day of April, 1994

*Attest:*

BRUCE LEHMAN

*Attesting Officer*     *Commissioner of Patents and Trademarks*